United States Patent [19]

Stewart et al.

[11] Patent Number: 4,885,464

[45] Date of Patent: Dec. 5, 1989

[54] IMPROVEMENTS RELATING TO A METHOD OF RADIOISOTOPE IMAGING

[75] Inventors: Peter A. E. Stewart, Bristol; Michael R. Hawkesworth, Birmingham, both of England

[73] Assignee: Rolls-Royce plc, England

[21] Appl. No.: 218,879

[22] Filed: Jul. 14, 1988

[30] Foreign Application Priority Data

Jul. 24, 1987 [GB] United Kingdom ................ 8717653

[51] Int. Cl.$^4$ ............................................. G01N 23/00
[52] U.S. Cl. ................... 250/308; 250/358.1; 250/473.1
[58] Field of Search ............... 250/475.2, 473.1, 303, 250/308, 363.03, 358.1, 307

[56] References Cited

U.S. PATENT DOCUMENTS

| | | | | |
|---|---|---|---|---|
| 3,769,511 | 10/1973 | Delacy | ................. | 250/303 |
| 4,463,263 | 7/1984 | Padawer | ................. | 250/308 |
| 4,697,079 | 9/1987 | Stewart et al. | ................. | 250/303 |

FOREIGN PATENT DOCUMENTS 815594 3/1981 U.S.S.R. ............................. 250/303

OTHER PUBLICATIONS

Bacon, "Radioactive Traces Used in Corrosion Studies", General Electric Review, May, 1949, pp. 7–9.

Primary Examiner—Carolyn E. Fields
Attorney, Agent, or Firm—Oliff & Berridge

[57] ABSTRACT

To produce an image of a component of part of an engineering structure such as an aero-engine using a positron emission tomography (PET) technique it is proposed to provide the component or part of the structure of interest with a surface coating containing a radioisotope labelling material. The radioisotope label may be provided by applying a film of lacquer, paint or the like containing the isotope, or the component etc. may be bombarded by suitably energetic ions in order to induce a reaction in which a selected isotope is produced.

6 Claims, No Drawings

IMPROVEMENTS RELATING TO A METHOD OF RADIOISOTOPE IMAGING

The invention relates to improvements to a method of radioisotope imaging, in particular, the invention relates to the technique known as positron emission tomography, or PET as it is commonly known.

Positrons are emitted by some radioisotopes as a characteristic part of their natural decay process. When a positron meets with an electron, within a very short time span after being emitted by a decaying nucleus, the two particles annihilate each other releasing two photons at characteristic energy levels of 511 keV. The two photons are emitted in opposite directions and are detected on opposite sides of the object being investigated.

The photon energy level at 511 keV is sufficient to penetrate a reasonable thickness of metal such as is likely to be encountered in a gas turbine aero-engine, for example. Gradually over the period of an exposure a picture is built up recording the distribution and density of the source of the positrons. The basic technique has been described previously, for example in UK Patent Application No. GB 2159380A "Analysing Fluid Flows within hollow bodies" when a fluid flow, such as lubrication oil, has been seeded with a radioisotope tracer. The metal parts of the structure are effectively invisible although some attenuation of the radiation does occur where the metal is thicker between the source and a detector. Computer models have been developed therefore to generate correction factors for compensating for the varying degrees of attenuation experienced by the radiation.

In these PET images, metal parts are invisible and only the seeded fluids appear in the detection system's image output, revealing the density and presence of the fluid, although to aid interpretation of these images a line drawing or like image of the engine is superimposed.

The present invention provides an improvement to the techniques mentioned above through the ability to generate images of parts of the engine, for example of gear teeth, in order to study wear, pick up and to provide a framework or outline image against which to study radioisotope labelled fluid flows.

According to the present invention a method of radioisotope imaging a mechnical structure comprises the step of providing a surface layer containing radioisotope material on at least a part of the structure in a region of interest.

As discussed above in known applications of positron emission tomography using seeded fluid flows within metal structures the metal parts are substantially invisible and although their presence and shape can be inferred in some cases from the shape of the fluid images, hitherto they have not been observable directly. In order to study these components directly while under test running conditions a surface coating is provided in at least the region of interest, such as gear teeth. The components, or part thereof so coated, then produce positron emissions to which the positron detectors respond producing images directly of the components themselves.

The resulting images can be used to observe wear, pick up and to provide a framework against which the radioisotope labelled flows can be analysed. Using image matching techniques accurate scaled drawings of the engine can be superimposed on the component images both for study of the components and of the fluid flows.

Radioisotope labelling of the components can be carried out by applying to the region of interest a lacquer or paint or like coating containing the radioisotope in liquid or particulate form. Alternatively, if it is wished to provide a surface coating integral with the surface of the component it may be labelled through bombardment with suitably energetic ions from a particle accelerator in order to induce an appropriate nuclear reaction in a surface layer.

In another surface coating process the active isotopes may be embedded in a surface layer by a deposition process or by a plating process. An active layer may also be overlayed by a plated coating, eg by vapour deposition, in order to protect a delicate active layer from abrasion or dissolution and also to provide a retarding layer to slow or stop positrons thus reducing the free path length before annihilation and photon emission occurs.

A preferred range of suitable positron emitting isotopes for use in an applied surface coating lacquer or the like includes those given by way of example in Table 1. The half-life of each isotope is indicated in each case.

TABLE 1

| Isotope | Half-life |
|---|---|
| 82 Rb | 1.3 minutes |
| 11 C | 20 minutes |
| 68 Ga | 68 minutes |
| 18 F | 110 minutes |
| 124 I | 4.2 days |
| 22 Na | 2.6 years |
| 45 Ti | 3.1 hours |
| 58 Co | 71 days |
| 65 Zn | 245 days |

Of those isotopes listed, by way of example, in the above table 82 Rubidium is able to be produced in copious quantities although it has only a relatively short half-life. 11 Carbon has a usefully longer half-life but it is still sufficiently short to permit quick handling of components which may sometimes be an advantage. In practice the isotopes of fluorine, iodine, sodium, titanium, cobalt and zinc are like to be embedded in the surface of an object by deposition methods. The isotopes or initial starting substance to produce a selected isotope (see Table 2 below) may be introduced by deposition either in or on the surface of a component, for example, by a vapour deposition process or by a plating process.

Suitable reactions for producing positron emitting surface layers integral with the component surface layers integral with the component surface are given in Table 2. Again the half-life of the resulting isotope is indicated in each instance.

TABLE 2

| Reaction | Product half-life |
|---|---|
| 11 B (p,n) 11 C | 20.3 minutes |
| 16 O (3He,p) 18 F | 110 minutes |
| 65 Cu (p,n) 65 Zn | 245 days |
| 56 Fe (p,n) 56 Co | 77 days |
| 52 Cr (p,n) 52 Mn | 2.7 days |
| 59 Co (p,3n) 57 Ni | 33 hours |
| 24 Mg (d,$\alpha$) 22 Na | 2.6 years |

The initial or starting isotopes for the reactions listed in Table 2 are commonly found in engineering metals and alloys, although the presence and proportion of a particular substance will depend upon the composition of a particular alloy. The indicated reactions may be produced by bombarding an object containing the selected starting isotope by the first mentioned particles, noted in parentheses, produced by a particle accelerator. The exact particle energy level required to produce the noted reaction varies between individual instances but are well understood and recorded in relevant literature. Generally energy levels in the range 10–20 MeV will be found useful but this can only be offered as a guide and the exact energy level required must be determined empirically, although because it is not normally possible to vary the output energy level of an accelerator the best available energy level only must be selected.

The examples given above in Table 1 and 2 are not to be construed as exhaustive. Further isotopes may be found suitable for addition to the range of isotopes given in Table 1 and further reactions additional to those given in Table 2 may be found to be compatible with PET techniques in engineering applications for the purposes of imaging components and structures directly.

We claim:

1. A method radioisotope imaging of a mechanical structure comprising the step of providing on at least part of the structure in a region of interest a surface layer in the form of an applied film containing radioisotope material selected from the group consisting of 68Ga, 18F, 124 I, 22Na, 45Ti, 58Co and 65Zn.

2. A method according to claim 1 wherein the radioisotope material is applied in liquid form.

3. A method according to claim 1 wherein the radioisotope material is applied in particulate form.

4. A method of radioisotope imaging of a mechanical structure comprising the step of providing on at least part of the structure in a region of interest a surface layer of radioisotope material formed by bombardment with suitably energetic ions of an initial isotope wherein the radioisotope material is produced by a reaction belonging to a group consisting of the reactions 65Cu (p,n) 65Zn, 56Fe (p,n) 56Co, 52Cr (p,n) 52(Mn, 59Co (p, 3n) 57Ni, and 24Mg (d,$\alpha$) 22Na.

5. A method according to claim 4 wherein the surface layer is produced by a deposition process.

6. A method according to claim 5 wherein the deposition process includes providing a plated layer.

* * * * *